(12) United States Patent
Bergens (10) Patent No.: US 9,937,297 B2
(45) Date of Patent: Apr. 10, 2018

(54) MEDICAMENT DELIVERY DEVICE

(71) Applicant: Carebay Europe Ltd, Swatar (MT)

(72) Inventor: Thomas Bergens, Ingarö (SE)

(73) Assignee: Carebay Europe Ltd, Sliema (MT)

( * ) Notice: Subject to any disclaimer, the term of this patent is extended or adjusted under 35 U.S.C. 154(b) by 404 days.

(21) Appl. No.: 14/783,866

(22) PCT Filed: Mar. 25, 2014

(86) PCT No.: PCT/EP2014/055983
§ 371 (c)(1),
(2) Date: Oct. 11, 2015

(87) PCT Pub. No.: WO2014/166735
PCT Pub. Date: Oct. 16, 2014

(65) Prior Publication Data
US 2017/0319793 A1     Nov. 9, 2017

(30) Foreign Application Priority Data

Apr. 12, 2013 (SE) .................................. 1350464

(51) Int. Cl.
*A61M 5/00* (2006.01)
*A61M 5/32* (2006.01)
*A61M 5/20* (2006.01)

(52) U.S. Cl.
CPC ............ *A61M 5/3287* (2013.01); *A61M 5/20* (2013.01); *A61M 5/3243* (2013.01); *A61M 5/3202* (2013.01); *A61M 2005/3241* (2013.01)

(58) Field of Classification Search
CPC .. A61M 2005/2407; A61M 2005/3126; A61M 5/31543; A61M 5/31575;
(Continued)

(56) References Cited

U.S. PATENT DOCUMENTS

| 2,585,815 A | 2/1952 | McLintock |
| 2010/0280461 A1 | 11/2010 | Forstreuter |
| 2012/0310168 A1* | 12/2012 | Plumptre .......... A61M 5/31543 604/189 |

FOREIGN PATENT DOCUMENTS

| EP | 1681070 A1 | 7/2006 |
| WO | 03/011371 A2 | 2/2003 |

(Continued)

OTHER PUBLICATIONS

EPO, Int'l Search Report in PCT/EP2014/055983, Aug. 6, 2014.

*Primary Examiner* — Phillip Gray
(74) *Attorney, Agent, or Firm* — Piedmont Intellectual Property (57) ABSTRACT

A medicament delivery device includes a housing; a hollow plunger rod; a dose drum concentrically arranged between the housing and plunger rod and movable when setting and delivering a dose; and a plunger rod driver. The driver includes a hollow ratchet arm drum movably arranged within the plunger rod and fixed to the dose drum, with the arm drum and rod releasably coupled; a dose activator having a longitudinal rod movably arranged within and releasably coupled to the arm drum; a dose setting knob fixed to the dose activator and releasably coupled to the arm drum; and a resilient element arranged between the arm drum and dose activator that biasses them in a direction decoupling the longitudinal rod from the arm drum and coupling the knob with the arm drum, such that during dose setting, turning the knob forces the arm drum and dose drum to rotate together.

15 Claims, 10 Drawing Sheets

(58) Field of Classification Search
CPC .. A61M 5/31585; A61M 5/3287; A61M 5/20; A61M 5/3243
USPC ........................................................ 604/235
See application file for complete search history.

(56) References Cited

FOREIGN PATENT DOCUMENTS

| | | |
|---|---|---|
| WO | 2004/078242 A2 | 9/2004 |
| WO | 2012/125876 A1 | 9/2012 |

* cited by examiner

Fig. 10

MEDICAMENT DELIVERY DEVICE

TECHNICAL FIELD

The present invention relates to a medicament delivery device and in particular a device capable of delivering a dose of medicament set by user before delivery.

BACKGROUND

There are numerous devices for delivering medicament on the market and also patented where the medicament is arranged in a container, such as a syringe, cartridge and the like, and wherein the medicament is exposed to pressure when it is to be delivered. A very common design is a generally tubular compartment having a stopper in one end of the compartment and a delivery member attached to the opposite end of the compartment, such as, e.g., a needle, a nozzle or the like member capable of delivering medicament to a patient.

In order to deliver a quantity of medicament, the stopper is exposed to pressure, i.e. pushed into the compartment by a plunger rod, which could be done manually by a finger, which is the case for simple handheld syringes, or by pressure means such as springs, which is common in automatic or semi-automatic injectors. In this context, the so called pen-injectors are becoming quite common, where the injection is performed by manually pushing at a distal end of the device. With this type of injector there has also been a development regarding delivering different dose quantities with the same device, i.e. to be able to set a certain prescribed dose before delivery.

A number of such devices have been developed, such as the device disclosed in EP-A-1 601 395. Here the device is arranged with a dose setting drum that can be rotated in relation to a housing and a drive sleeve that, upon manual operation by a user, drives a plunger rod to deliver a set dose of medicament. In order to provide the function of setting a dose with the dose setting drum and delivering a dose with the drive sleeve, there has to be some sort of connection/disconnection mechanism between them. Thereby a clutch or uni-directional connection mechanism has been developed for providing the desired function. This solution entails a number of components that are to interact with each other as well as a number of threaded engagement and connection mechanisms that require careful design in order for the manually applied force by a user not to be too large, or the device otherwise will not function properly. There is also a question whether the solution according to EP-A-1 601 395 can provide the possibility of resetting a set dose in a simple and efficient manner.

Another feature with the device of EP-A-1 601 395 is that the setting of a dose larger than the remaining quantity should be prevented in that when a nut reaches the end of a helical thread of the connection mechanism, the nut stops rotating of a dose dial sleeve and the drive sleeve will thus become locked together preventing rotation of the dose dial sleeve and setting of a larger dose. This direct action between threads is not so precise in that there is no distinct stop between the components. Rather, the components could be turned in relation to each other quite a turning distance before the friction becomes so high that it is difficult to turn them relative each other any longer. Thus, a user could then erroneously believe that he/she is receiving a larger dose than the actual dose received.

Further, the components, such as the dose setting drum and the drive sleeve as well as the plunger rod are elongated and positioned inside each other. In order to not risk a jamming between the components, a certain play is necessary. Then, such play and gaps between components increase the risk of lack of support and therefore rattling and other noises that may negatively affect a potential user.

SUMMARY

An object of the present invention is to provide a medicament delivery device wherein the drawbacks of the state of the art devices are remedied.

In order to overcome one or several of the above-mentioned problems, a medicament delivery device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site. Further, the term "longitudinal", with or without "axis", refers to a direction or an axis through the device or components thereof in the direction of the longest extension of the device or the component. In a similar manner, the term "transversal", with or without "axis", refers to a direction or an axis through the device or components thereof in a direction generally perpendicular to the longitudinal direction. Also, if nothing else is stated, in the following description wherein the mechanical structure of the device and the mechanical interconnection of its components is described, the device is in an initial non-activated or non-operated state.

The invention provides a medicament delivery device, comprising a housing having a proximal end and a distal end; a hollow plunger rod being arranged within the housing; a telescopic dose drum being concentrically arranged between the housing and the plunger rod, the telescopic dose drum being bidirectional movable in relation to the housing and in relation to the plunger rod when setting a dose and delivering a dose; and plunger rod driving means for driving the hollow plunger rod towards the proximal end. The plunger rod driving means may comprise: a hollow ratchet arm drum being movably arranged within the hollow plunger rod and being fixedly connected to the telescopic dose drum, wherein the hollow ratchet arm drum and the hollow plunger rod are releasably coupleable to each other; a dose activator having a longitudinal rod being movably arranged within the hollow ratchet arm drum, wherein the longitudinal rod and the hollow ratchet arm drum are releasably coupleable to each other; a dose setting knob being fixedly connected to the dose activator and being releasably coupleable to the hollow ratchet arm drum; and a resilient element arranged between the hollow ratchet arm drum and the dose activator biasing them in a direction decoupling the longitudinal rod of the dose activator from the hollow ratchet arm drum and coupling the dose setting knob with the hollow ratchet arm drum, such that during a dose setting, turning of the dose setting knob by a user forces the hollow ratchet arm drum and the telescopic dose drum to rotate together.

Preferably, the longitudinal rod and the hollow ratchet arm drum are configured to couple each other against the biasing of the resilient element if, after a dose is set, axial movement of the dose activator is made towards the proximal end by a user, thereby the hollow ratchet arm drum and the hollow plunger rod also to couple together so that the hollow plunger rod and the telescopic dose drum can be displaced towards the proximal end for delivering the set dose.

Further, the resilient element may be configured, after delivery of the set dose, to force the dose activator towards the distal end, so that the dose setting knob and the hollow ratchet arm drum couple each other and the longitudinal rod and the hollow ratchet arm drum decouple each other, thereby also decoupling the hollow ratchet arm drum and the hollow plunger rod for setting a new dose.

In addition, the resilient element may include a spring element interposed between the hollow ratchet arm drum and the dose activator forcing them to move away from each other.

Moreover, the dose setting knob may be configured, by the axial movement of the dose activator towards the proximal end, to be decoupled from the hollow ratchet arm drum so that the dose setting knob does not rotate while the dose drum rotates for delivering the dose.

Furthermore, the dose setting knob may include locking knobs shaped to match corresponding rotation locks arranged on the hollow ratchet arm drum.

Additionally, the resilient element may be arranged to bias the locking knobs of the dose setting knob to be coupled with the rotation locks of the hollow ratchet arm drum, so that the dose setting knob and the hollow ratchet arm drum can rotate together.

Besides, the device may further comprise a step driver rotationally fixed but axially movable in relation to the housing, wherein the step driver comprises first slanted guide ribs interfacing with a corresponding structure of the dose drum whereby when the dose drum rotates during the dose setting, the corresponding structure slides over the first slanted guide ribs, thereby producing audible and/or tactile information.

Herein, the corresponding structure of the dose drum may be second slanted guide ribs.

Further, the telescopic dose drum may include a distal part and a proximal part being slidably arranged relative to each other, wherein the distal part is arranged coaxially radially outside of the proximal part.

In additional, the second slanted guide ribs may be arranged on a proximal end of the proximal part.

Moreover, the step driver may further include at least one refracting arm for holding the proximal part, which is configured to retract the proximal part to sustain fixed increments during a dose setting.

Furthermore, the device may further comprise a dose blocker member being rotationally and axially fixed to the plunger rod, wherein said dose blocker member is configured to interact with a stop member on said proximal part when the set dose equals the remaining dose in the medicament container such that rotation of the telescopic dose drum is inhibited.

Besides, said dose blocker member may have a ring-shaped body comprising at least one stepped portion on its surface facing towards the proximal end.

Additionally, the at least one stepped portion may be configured, as the plunger rod moves axially, to engage a radial stop as the stop member, the radial stop being arranged on the inner surface of said proximal part so as to prevent a dose setting larger than remaining dose in a cartridge.

Other aspects, features, and advantages will be apparent from the summary above, as well as from the description that follows, including the figures and the claims.

The figures below disclose an embodiment of the invention for illustrational purposes only. In particular, the disclosure within the figures is not meant to limit the range of protection of the invention. The embodiment shown may be modified in many ways within the scope of the claims.

BRIEF DESCRIPTION OF THE DRAWINGS

FIG. 7a shows a cross-sectional view of the medicament delivery device according to FIG. 1;

FIG. 7b shows an enlarged view of the area within the circle indicated in FIG. 7a;

DETAILED DESCRIPTION

Mechanical Structure of an Embodiment

Figure 1:
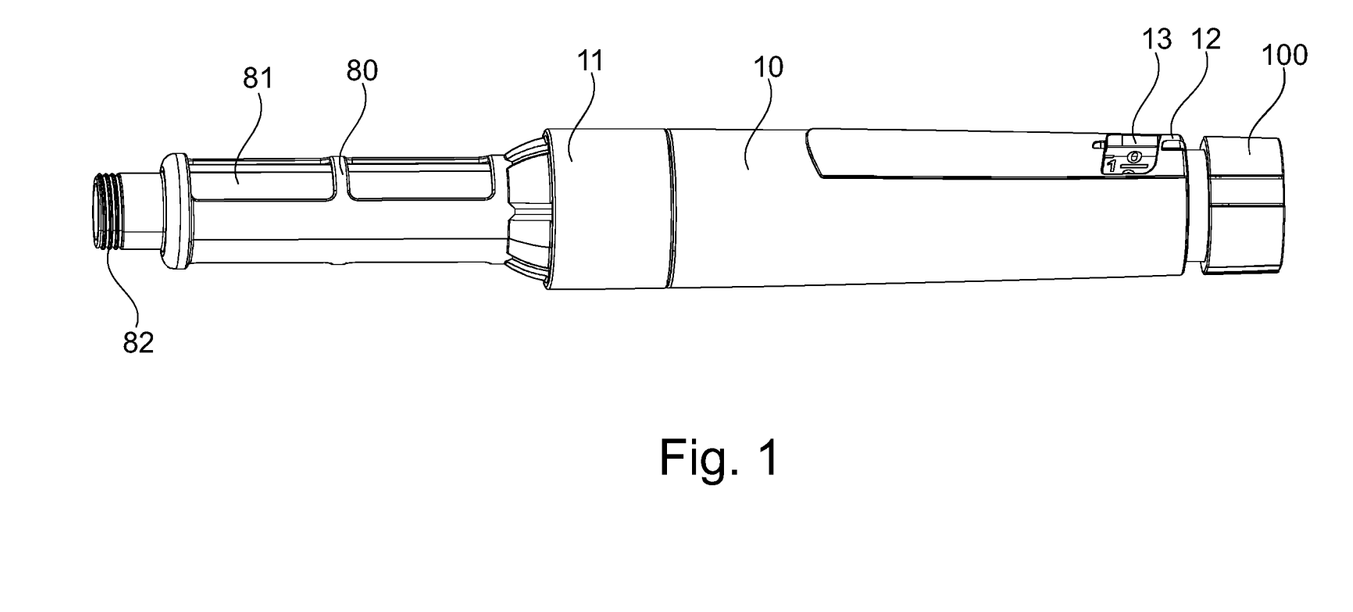
FIG. 1 shows a perspective view of a medicament delivery device according to a preferred embodiment of the invention, shown in the initial state.

FIG. 1 shows a perspective view of a medicament delivery device according to a preferred embodiment of the invention. The medicament delivery device has a proximal end and a distal end and comprises a housing 10 having a proximal part or end 11 and a distal part or end 12. In the assembled state of the medicament delivery device, the housing 10 forms part of the outer surface or appearance of the medicament delivery device. It is however to be understood that the housing may be designed in many other ways.

The medicament delivery device further comprises a medicament container holder 80 which accommodates a medicament container. The medicament container holder 80 also forms part of the outer surface or appearance of the medicament delivery device. The proximal part of the container holder 80 is further arranged with a neck 82 at its proximal end for attaching a per se known and conventional injection needle (not shown). It is however to be understood that other types of connection members, such as bayonet fitting Luer-lock fittings and the like may be arranged. Also, the medicament container may have an injection needle integrated in its body whereby the neck portion 82 may be omitted.

A cap (not shown) may be provided for releasably covering the proximal end of the device, and thereby the proximal end of the medicament container holder 80, when not in use.

The medicament container holder 80 of the medicament delivery device comprises a window 81 that allows the user to view the progress of medicament delivery, i.e. whether the medicament delivery device is still in its initial stage with the medicament not yet being injected, or whether the medicament container is already emptied. Through window 81, the user can see the medicament container accommodated at least in the medicament container holder 80 (the distal part of the medicament container may reach into the proximal part of the housing 10). In a preferred embodiment, such windows are provided at opposite sides of the medicament container holder 80.

Furthermore, at the distal end 12 of the housing 10, a further window 13 is provided that is used to indicate a set dose to a user, as described in more detail below. At the distal end 12 of housing 10, a dose setting knob 100 for dose setting projects distally.

Figure 2:
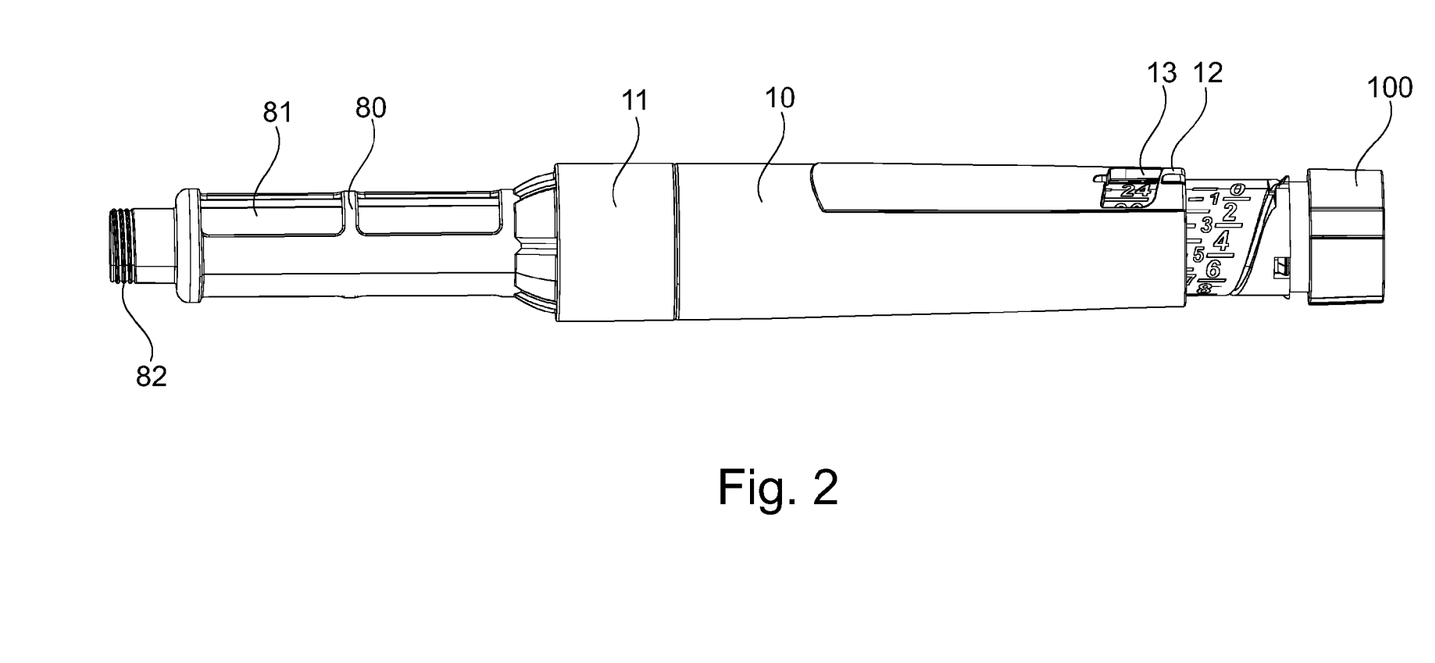
FIG. 2 shows a perspective view of a medicament delivery device according to the preferred embodiment of FIG. 1, shown in the state when a dose is set.

FIG. 1 shows the medicament delivery device in the initial state. When the user grasps the dose setting knob 100 and rotates it in a first direction, for example in clockwise direction, the dose setting knob 100 and other components move distally, as will be explained in detail below, in order to set a dose. FIG. 2 shows a perspective view of the medicament delivery device in such state, i.e. when a dose is set.

Figure 3:
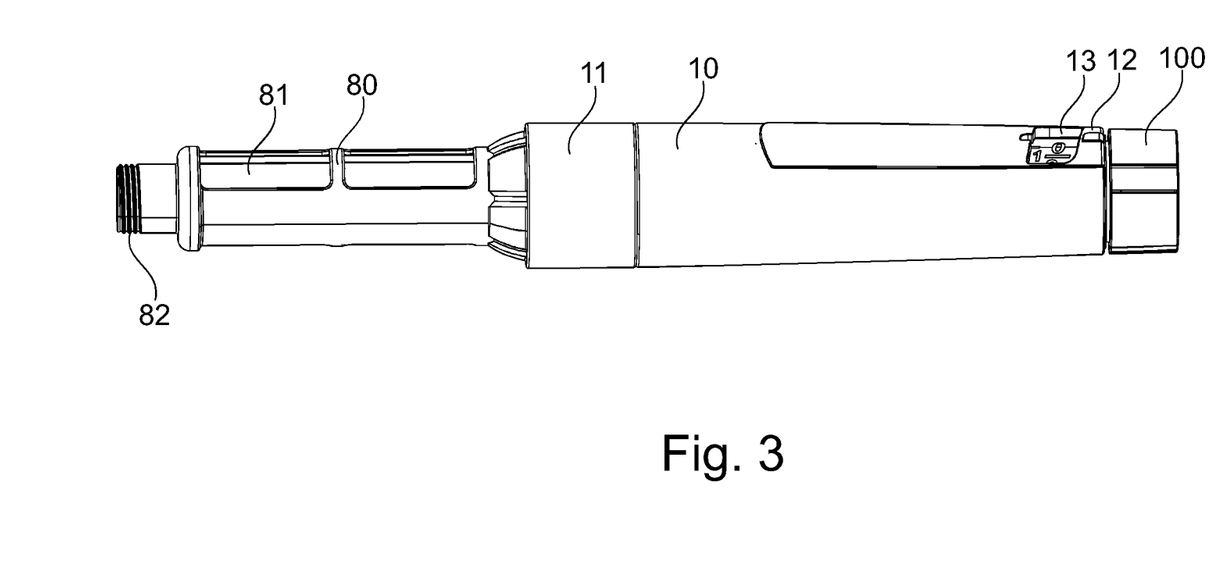
FIG. 3 shows a perspective view of a medicament delivery device according to the preferred embodiment of FIG. 1, shown after a set dose has been delivered.

FIG. 3 shows a perspective view of the medicament delivery device after a set dose has been delivered. As can be seen, the dose setting knob 100 and the components linked therewith were moved proximally and the dose setting knob 100 is again in its initial position. However, the plunger rod 20 of the medicament delivery device has been displaced in proximal direction and a stopper 29 within the medicament container has been also moved in the same direction.

The medicament container holder 80 is arranged with attachment means for connecting or attaching it to the proximal housing part 11. In the embodiment shown the attachment means comprise a protrusion (not shown) fitting into a corresponding recess 14. It is however to be understood that other attachment members may be utilized, such as bayonet fittings, threads, or the like for attaching the medicament container holder 80 with the housing 10.

An elongated plunger rod 20 (see FIGS. 4 to 6) is arranged inside the housing 10 and has a longitudinal axis generally corresponding with the longitudinal direction of the medicament delivery device. The plunger rod 20 is arranged with threads 21 on at least part of its outer surface. In the preferred embodiment shown in the drawings, the plunger rod 20 comprises a threaded structure 21 on its outer surface. Further, the plunger rod 20 comprises at least one longitudinal groove 25 (In the shown embodiment, two such grooves 25 are provided at opposite sides). The proximal end of the plunger rod 20 is arranged with a washer or spinner 28, (FIG. 4) adapted to abut the stopper 29. The stopper 29 is intended to be movably received inside the medicament container 85.

Figure 4:
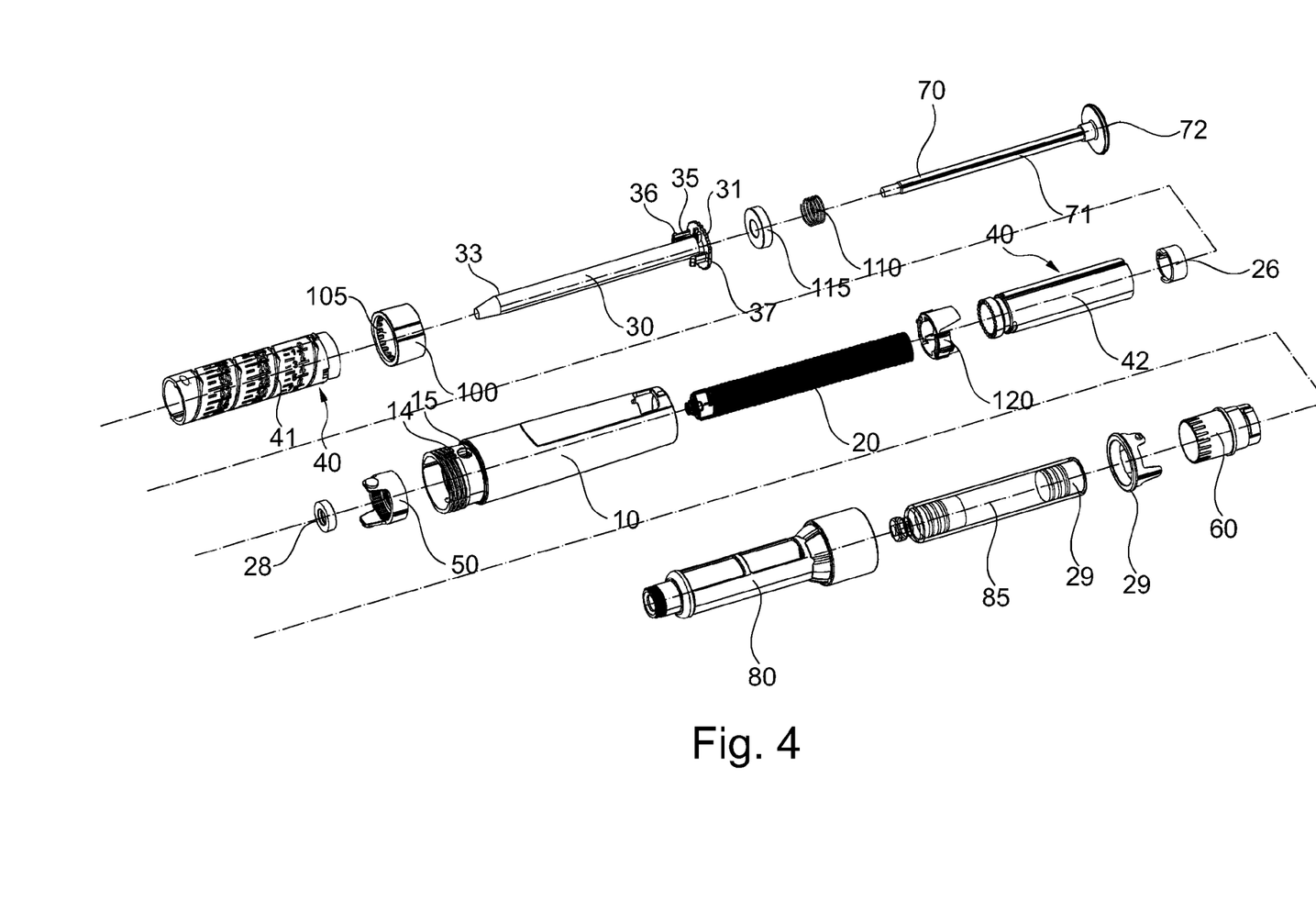
FIG. 4 shows an exploded view of the medicament delivery device according to the preferred embodiment of FIG. 1.

The plunger rod 20 fits into an insert 50 arranged with a central passage 51, (FIG. 6) the center of which generally coincides with the longitudinal axis of the medicament delivery device. The central passage 51 of the thread insert is arranged with threads 52 of complementary design as the threads 21 of the plunger rod 20. The outer surface of the insert 50 comprises at least one protrusion 53 or the like, fitting into corresponding recesses 15 (FIG. 4) on the inner surface of the housing 10, whereby the insert 50 is locked to the proximal housing part 11. As shown in FIG. 4, recess 15 in the housing may be formed as a through hole.

The insert 50 further comprises a central bore 54 at the proximal side of the thread insert 50. The diameter of the central bore 54 is larger than the diameter of the central passage 51 so that a stepped configuration is provided. The inner circumferential surface of the central bore 54 is arranged with a circumferentially extending ratchet 55 arranged with saw-tooth shaped teeth.

Figure 6:
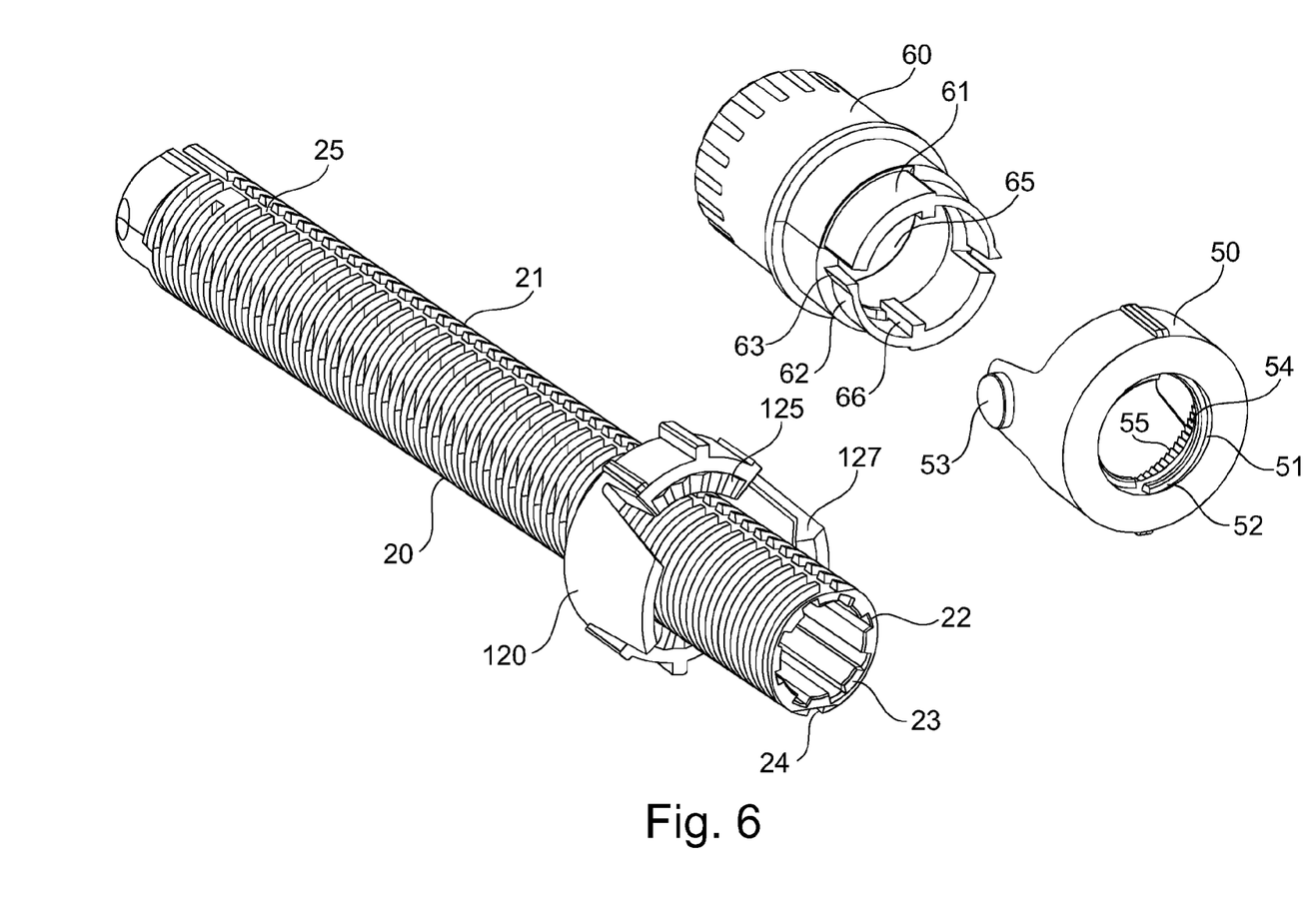
FIG. 6 shows another partly exploded view of the medicament delivery device according to FIG. 1.

The ratchet 55 cooperates with a ring-shaped back rotating blocker 60 (FIG. 6) which is arranged with two oppositely positioned resilient tongues 62, extending on the outer circumferential surface 61 generally in the circumferential direction of the blocker 60. Although two such tongues 62 are shown in FIG. 6, a single tongue may as well suffice, or more than two tongues may be provided, depending on the size of the blocker 60. The one or more tongues 62 are flexible in the generally radial direction. On the outwardly directed surfaces of the tongue(s) 62, a ledge 63 is arranged. Each ledge 63 has a shape complementary to the ratchet 55 of the thread insert 50. The back rotating blocker 60 is further arranged with a central passage 65 (FIG. 6) through which the plunger rod 20 extends. The central passage 65 is arranged with radially inwardly directed protrusions or ribs 66, which protrusions 66 fit into the elongated grooves 25 on the outer surface of the plunger rod 20. This structure provides a rotational lock of the plunger rod 20 but allows a movement of the plunger rod 20 in the longitudinal direction.

The plunger rod 20 is further arranged with a plurality of longitudinal splines or ribs 23 provided on the inner circumferential surface 22 of the hollow plunger rod 20 (FIG. 6). A ratchet arm drum 30 (FIG. 4) of generally tubular shape is arranged radially inside the plunger rod 20. The ratchet arm drum 30 is provided with a distal end wall 31 transversal to the longitudinal axis of the ratchet arm drum 30. The distal end wall 31 has central opening and the ratchet arm drum is hollow in order to receive a dose activator 70 therein, as will be described below. The proximal end of the ratchet arm drum 30 comprises one or more, preferably two, flexible arms 33 extending in the proximal direction. The arms 33 are flexible in that their proximal ends are radially deflectable upon application of a radial force thereon, as will be describe below. The outer surface of each flexible arm 33 comprises a radially projecting plunger rod engagement surface 34 (FIG. 7b) for selectively engaging with the longitudinal splines 23 on the inner surface 22 of the plunger rod 20. The shape of the surface 34 may generally correspond to the shape of the circumferentially arranged ribs 23 on the plunger rod 20. The inner surface of each flexible arm 33 comprises a radial engagement protrusion 37 (FIG. 7b) for selective engagement with the dose activator 70 located within the hollow ratchet arm drum 30.

The distal end wall 31 forms a coupling element by means of two proximally extending locking arms 35 (FIG. 4). The locking arms 35 comprise at their respective outer surface a locking structure 36 for locking the ratchet arm drum 30 to the inner surface of the dose drum 40. Along the outer circumference of the distal end wall 31 is provided rotation locks 37 of a toothed shape, which is configured to correspond with locking knobs 105 formed along an inner circumferential surface of the tubular-shaped dose setting knob 100. As described in more detail below, engagement/disengagement between the rotation locks 37 and the locking knobs 105 provides secure locking/unlocking of the dose setting knob 100 in relation to the ratchet arm drum 30.

Figure 5:
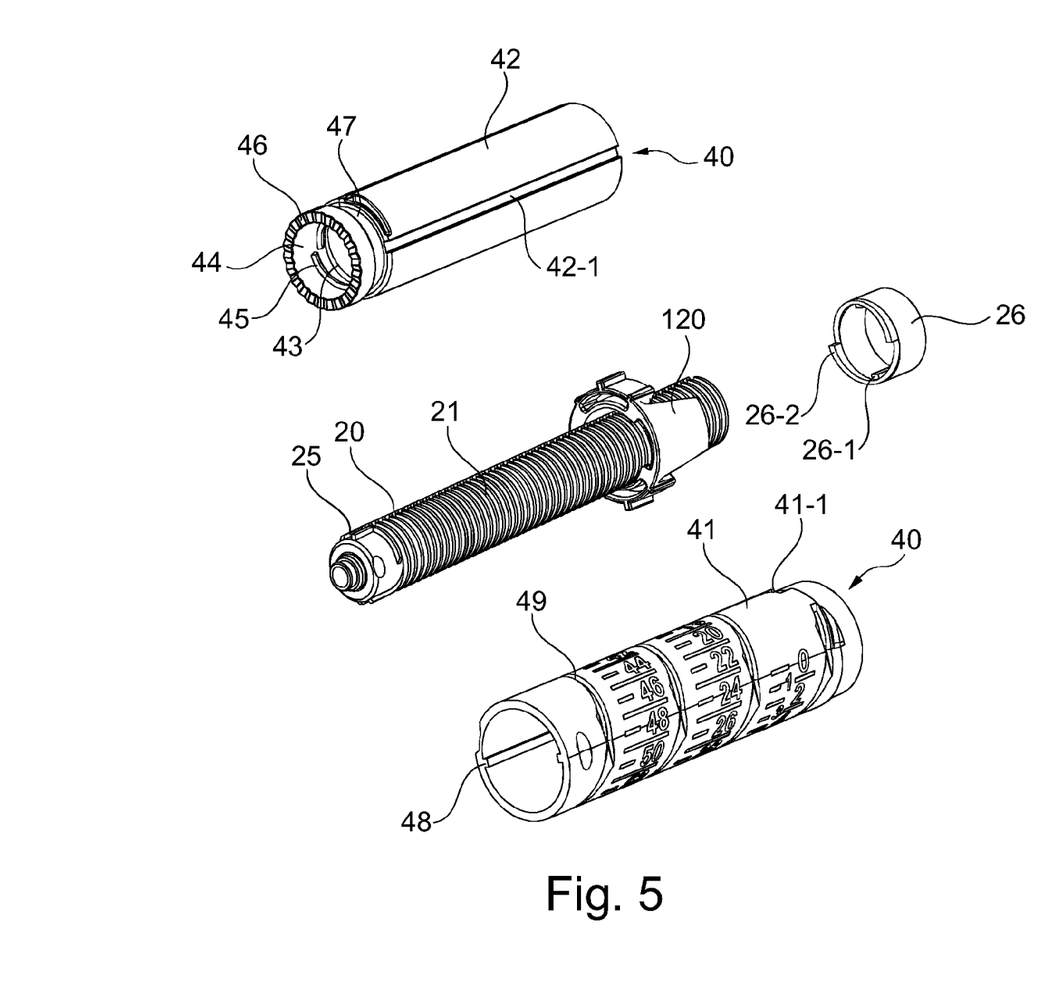
FIG. 5 shows a partly exploded view of the medicament delivery device according to FIG. 1.

Outside the plunger rod 20 as seen in a radial direction, a telescopic dose (setting) drum 40 is arranged (FIGS. 4 and 5). The dose drum 40 has a generally tubular shape and is positioned coaxially with the plunger rod 20 as well as the housing 10. The dose drum 40 comprises a first, distal, part 41 and a second, proximal, part 42 being slidably arranged relative to each other. The distal part 41 is located coaxially radially outside of the proximal part 42 of the dose drum 40.

The distal part 41 comprises a helically or spirally extending groove 49 (FIG. 5) on its outer side surface. The groove 49 extends all the way from the proximal end to the distal end of the distal part 41 of the dose drum 40. The groove 49 is intended to cooperate with at least one protrusion or spirally extending ledge segment (not shown) arranged on the inner surface of the housing 10 such that the dose drum 40 is rotationally connected to the housing 10, whereby mutual rotation causes movement in the longitudinal direction of the parts. The distal end area of the first part 41 of the dose drum 40 is further arranged with a locking structure, e.g., recesses 41-1 for axial stop, that engages with the locking structure 36 of the ratchet arm drum 30 when the ratchet arm drum 30 is moved into the plunger rod 20 during assembly of the medicament delivery device.

Figure 8:
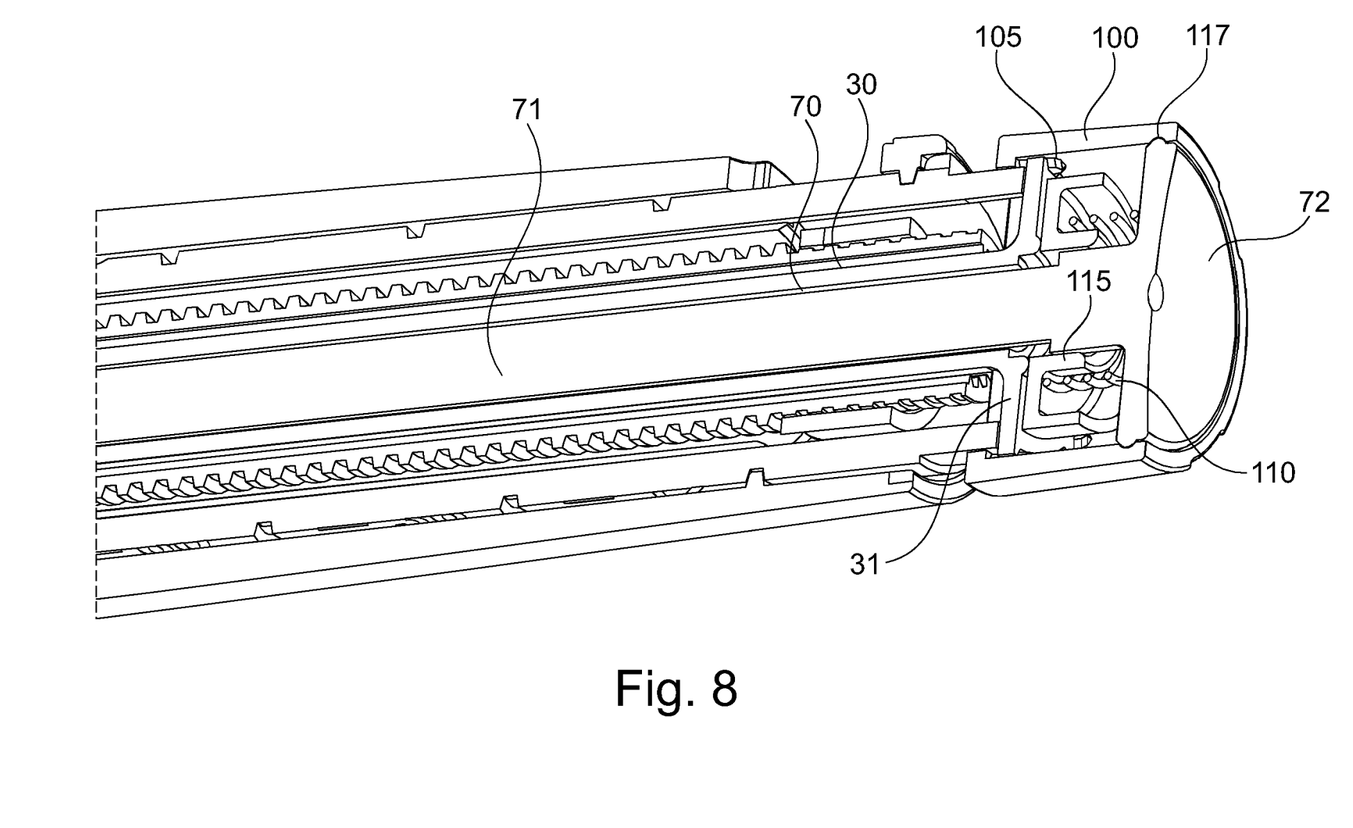
FIG. 8 shows a partial cross-sectional view of the medicament delivery device according to FIG. 1, shown in the initial state.
Figure 9:
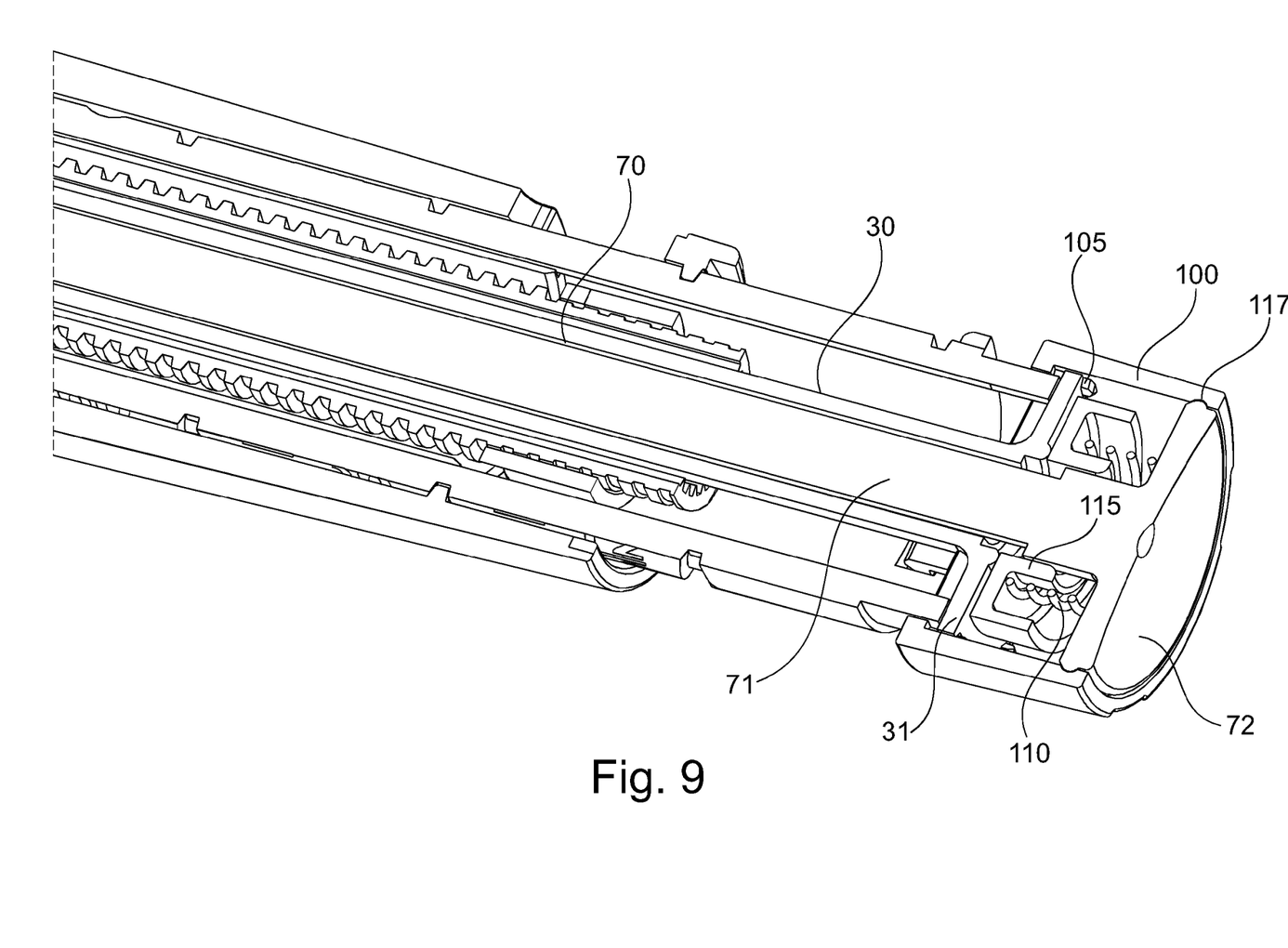
FIG. 9 shows a partial cross-sectional view of the medicament delivery device according to FIG. 1, shown in the state when a dose is set

At the distal end of the first part 41 the dose setting knob 100 is arranged (FIGS. 4, 8 and 9). The dose setting knob 100 comprises a generally tubular part having a diameter somewhat larger than the outer surface of the first part 41 of the dose drum 40. Along the inner surface of the dose setting knob 100, the first part 41 of the dose drum 40 can move proximally and/or distally during the dose setting and injection processes. Herein, since the ratchet arm drum 30 is axially locked with the first part 41 by the engagement between the locking structures 41-1 and 36, depending on the relative axial movement between the first part 41 and the dose setting knob 100, the rotation locks 37 of the ratchet arm drum 30 becomes selectively engaged or disengaged with the locking knobs 105 provided at the proximal end of the dose setting knob 100, as best illustrated in FIGS. 8 and 9. In the meantime, the outermost diameter of the dose setting knob 100 is preferably flush with the outer diameter of housing 10. The first part 41 of the telescopic dose drum 40 is thus configured to rotationally move distally in the first direction relative to the housing 10 during dose setting by the dose setting knob 100.

The inner circumferential surface 44 of the second part 42 of the telescopic dose drum 40 is threadedly connected to the threaded outer circumferential surface 21 of the plunger rod 20. In particular, the proximal end of the second part 42 comprises a threaded structure 45 (FIG. 5). The threaded connection between the first part 41 of the telescopic dose drum 40 and the inner circumferential surface of the housing 10 has a pitch different to the pitch of the threaded connection of the inner circumferential surface 44 of the second part 42 of the telescopic dose drum 40 and the threaded outer circumferential surface 21 of the plunger rod 20.

The device further comprises a step driver 120 being rotationally fixed but axially movable in relation to the housing 10 and interacting with the second part 42 of the dose drum 40 in order to produce audible and/or tactile information during turning of the dose drum 40 for a dose setting. The step driver 120 is generally ring-shaped and provided with slanted guide ribs 125 on one side surface thereof facing the distal end of the device. Corresponding slanted guide ribs 46 are also formed on one side surface of the second part 42 of the dose drum 40 that faces the proximal end of the device, whereby the two corresponding slanted guide ribs 125 and 46 slide over each other and provide a distinct "click-feeling (sound)" for each dose size increment. Additionally, in order to sustain fixed dose size increment, the step driver 120 is provided with two oppositely positioned flexible retracting arms 127 for retracting the second part 42 of the dose drum 40. The flexible retracting arms 127, extending on the outer circumferential surface of the step driver 120 generally in the longitudinal direction of the device, hold the second part 42 of the dose drum 40 by riding on and interacting with a circumferential groove 47 formed on the outer circumferential surface of the second part 42 near the proximal end thereof.

The dose blocker ring 26 is a generally ring-shaped body (FIG. 5) comprising at least one longitudinally extending rib 26-1 on its inner surface. In this connection, the plunger rod 20 comprises at least one groove 24 (FIG. 6) on its outer circumferential surface at a distal portion thereof, which corresponds to the longitudinal rib 26-1 arranged on the blocker ring 26. By the engagement between the ribs 26-1 on the blocker ring 26 and the grooves 24 on the plunger rod 20, the dose blocker ring 26 is rotationally and axially fixed to the plunger rod 20. Meanwhile, the blocker ring 26 further includes a radial stop, e.g., at least one (two, in the embodiment shown) stepped portion 26-2 arranged on its surface facing towards the proximal end of the device, which is configured to interact with a corresponding radial stop 43 arranged on the inner surface of said second part 42 of the telescopic dose drum 40 when the set dose equals the remaining dose in the medicament container such that rotation of the telescopic dose drum 40 is inhibited.

Figures 7A, 7B:
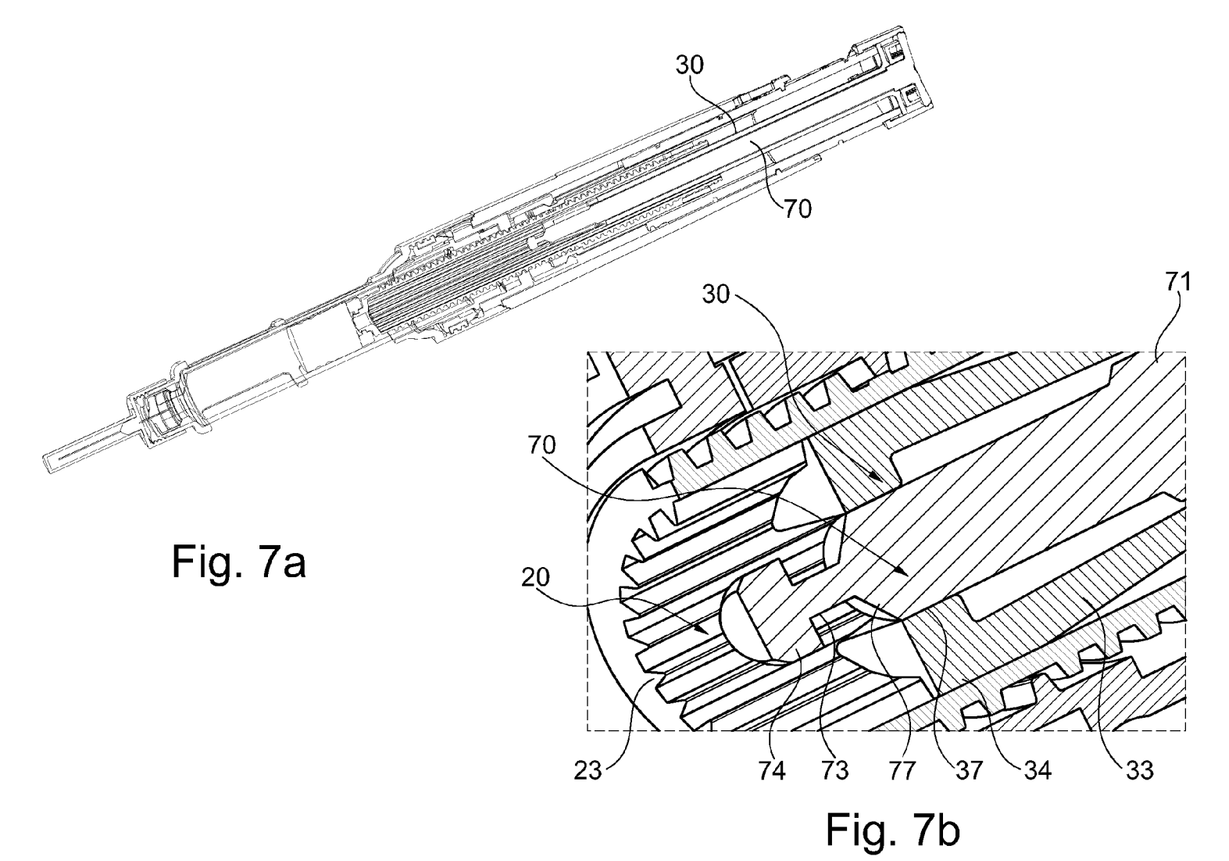

The dose activator 70 comprises a longitudinal rod 71 and a distal push button 72. The push button is intended to act as a contact surface for a finger of a user during drug delivery, as will be described. As described above, the longitudinal rod 71 of the dose activator 70 is accommodated within the hollow ratchet arm drum 30. At its proximal end, the longitudinal rod 71 comprises an engagement structure comprising a circumferential groove 73 (FIG. 7b). Adjacent the groove and in the proximal direction is a protrusion 74 and in the distal direction an inclined surface 77. The size of the groove 73 and the location on the longitudinal rod 71 is such that the radially inwardly directed protrusion 37 on the flexible arms 33 of the ratchet arm drum 30 is initially received in the groove 73. In such initial stage, the flexible arms 33 are not deflected radially outwards but are in a tension-free state.

The axial length of the dose activator 70 in comparison to the ratchet arm drum 30 is such that in the initial state of the medicament delivery device, i.e. with the engagement protrusion 37 being received in the groove 73, the proximal surface of the push button 72 is spaced from the distal surface of the distal end wall 31 by a gap 76 (see, e.g., FIG. 8). According to the preferred embodiment, within the gap 76 may be arranged a resilient element 110 and a holder 115 therefor, which will be described in detail below. The resilient element 110 forces the push button 72 in the distal direction and maintains the gap 76. Accordingly, in this specific embodiment the gap 76 may actually mean the gap between the push button 72 and the holder 115. This gap 76 is maintained when a dose is set by a user and the first part 41 of the dose drum 40, the ratchet arm drum 30 and the dose activator 70 are moved distally.

However, as soon as the push button 72 is pushed towards the proximal direction, the push button 72 first bridges the gap 76 thereby moving the longitudinal rod 71 in proximal direction relative to the ratchet arm drum 30. Due to such relative displacement, the inclined surface 77 is moved in contact with, and is pressed against, the engagement protrusion 37 on the flexible arms 33, thus deflecting the arms 33 outwardly and into engagement with the longitudinal splines on the inner surface 22 of the plunger rod 20.

Once a set dose is delivered, it is desirable for the dose activator 70 to move back distally in relation to the ratchet arm drum 30 and the first part 41 of the dose drum 40 so that the gap 76 between the proximal surface of the push button 72 and the distal surface of the distal end wall 31 can be secured again for another injection. For this end, the resilient element, i.e., a dose activator spring 110 in the preferred embodiment, and the spring holder 115 are arranged between the ratchet arm drum 30 and the dose activator 70, that is, between the proximal surface of the push button 72 and the distal surface of the distal end wall 31, to be more specific. The dose activator spring 110, being mounted on the spring holder 115 arranged on the distal surface of the coupling element 31, is configured to act on the proximal surface of the push button 72 forcing it in the distal direction, thereby decoupling the longitudinal rod 71 of the dose activator 70 from the hollow ratchet arm drum 30. Accordingly, as soon as a set dose is delivered and a user releases the push button 72, the push button 72 goes back to its initial position by the biasing force from the spring 110, thereby securing the gap 76.

In the meantime, the dose activator 70 is axially locked with respect to the dose setting knob 100 by being snap-in fastened into a groove 117 formed at the distal end on the inner surface of the dose setting knob 100. Accordingly, the axial movement of the push button 72 made by a user operation results in an axial movement of the dose setting knob 100 together with the dose activator 70 in the proximal/distal direction. After all, this axial movement of the dose setting knob 100 relative to the dose drum 40 brings about locking/unlocking of the dose setting knob 100 in relation to the ratchet arm drum 30 as aforementioned.

Description of the Function and Operation of the Embodiment

Setting Operation for a Dose to be Delivered

FIG. 8 shows a cross-sectional view of the medicament delivery device in the initial state.

In order for a dose to be delivered, the device must be operated to set a dose. In order to set a dose to be delivered the user grips the housing 10 and the distally arranged dose setting knob 100 and turns them in relation to each other, where the dose setting knob 100 is turned in the clockwise direction, for example. The turning of the dose setting knob 100 will cause the ratchet arm drum 30 to be rotated together due to the their engagement through the rotation locks 37 and the locking knobs 105. This in turn causes the first part 41 of the dose drum 40 to be rotated because the first part 41 is again rotationally locked with the ratchet arm drum 30, as explained above. Due to the connection between the helical groove 49 of the dose drum 40 and the spiral ledge segment of the housing 10, the rotation will cause the first part 41 of the dose drum 40 to move in the distal direction in relation to the housing 10.

The longitudinal ribs 48 on the inner surface of the first part 41 of the dose drum 40 are in contact with the longitudinal grooves 42-1 on the outer surface of the second part 42 of the dose drum 40. Thus, the first part 41 can slide relative to the second part 42. Furthermore, the second part 42 is also rotated and due to the threads 45 engaging into the threaded surface of the plunger rod 20, the second part 42 also moves distally, albeit at a lower speed than the first part 41 due to the different pitches. As the second part 42 rotates, it interacts with the step driver 120 which is rotationally fixed to the housing 10, thereby generating audible and/or tactile information during the turning of the dose setting knob 100 for a dose setting. Rotation of the second part 42 also causes a certain turning force on the plunger rod 20, which also urges the back rotating blocking element 60 to turn due to the rotational lock between the blocking element 60 and the plunger rod 20 because of the protrusions 66 of the back rotating blocking element 60 fitting into the longitudinal grooves 25 of the plunger rod 20. However, the arms 62 of the back rotating blocking element 60 are directed such and cooperating such with the ratchet 55 of the thread insert 50 that any rotation of the back rotating blocking element 60 is prevented. Thus the plunger rod 20 is prevented from rotating. During rotation, preferably indicia (not shown) on the dose drum 40 are shown through the window or opening 13 at the distal end 12 of the housing 10. The patient thus rotates the dose setting knob 100 until the prescribed dose quantity is displayed.

If the user by mistake has set a too large dose, he/she simply turns the dose setting knob 100 in the opposite direction, whereby both the dose drum 40 and the ratchet arm drum 30 are turned in the opposite direction until the correct dose has been reached.

FIG. 9 shows a cross-sectional view of the medicament delivery device in the state when a dose is set. In particular, it can be seen that the gap 76 still exists.

Delivery Operation of a Pre-Set Dose of Medicament

In order to deliver a dose of medicament, the user presses the proximal end of the device against a dose delivery site, and in particular an injection site when the medicament delivery member is an injection needle. The next step is to press on the activator button 72 at the distal end of the device. This causes the gap 76 to close due to the force applied by the user and the button 72 contacts the distal end wall 31 of the ratchet arm drum 30.

The force on the activator button 72 will first bring the ratchet arm drum 30 into engagement with the inner surface of the plunger rod 20, as already described above. Secondly, once the gap 76 has been bridged, the force on the activator button 72 urges the dose drum 40 in the proximal direction and due to the threaded connection with the housing 10, the dose setting drum 40 will rotate, now in the anti-clockwise direction, and move in the proximal direction.

Because of the rotational lock between the dose drum 40 and the ratchet arm drum 30, the latter will also rotate. Due to the radial flexing of the arms 33 of the ratchet arm drum 30, the radially outwardly directed surface 34 of the ratchet arm drum 30 firmly engage the splines 23 of the plunger rod 20.

Figure 10:
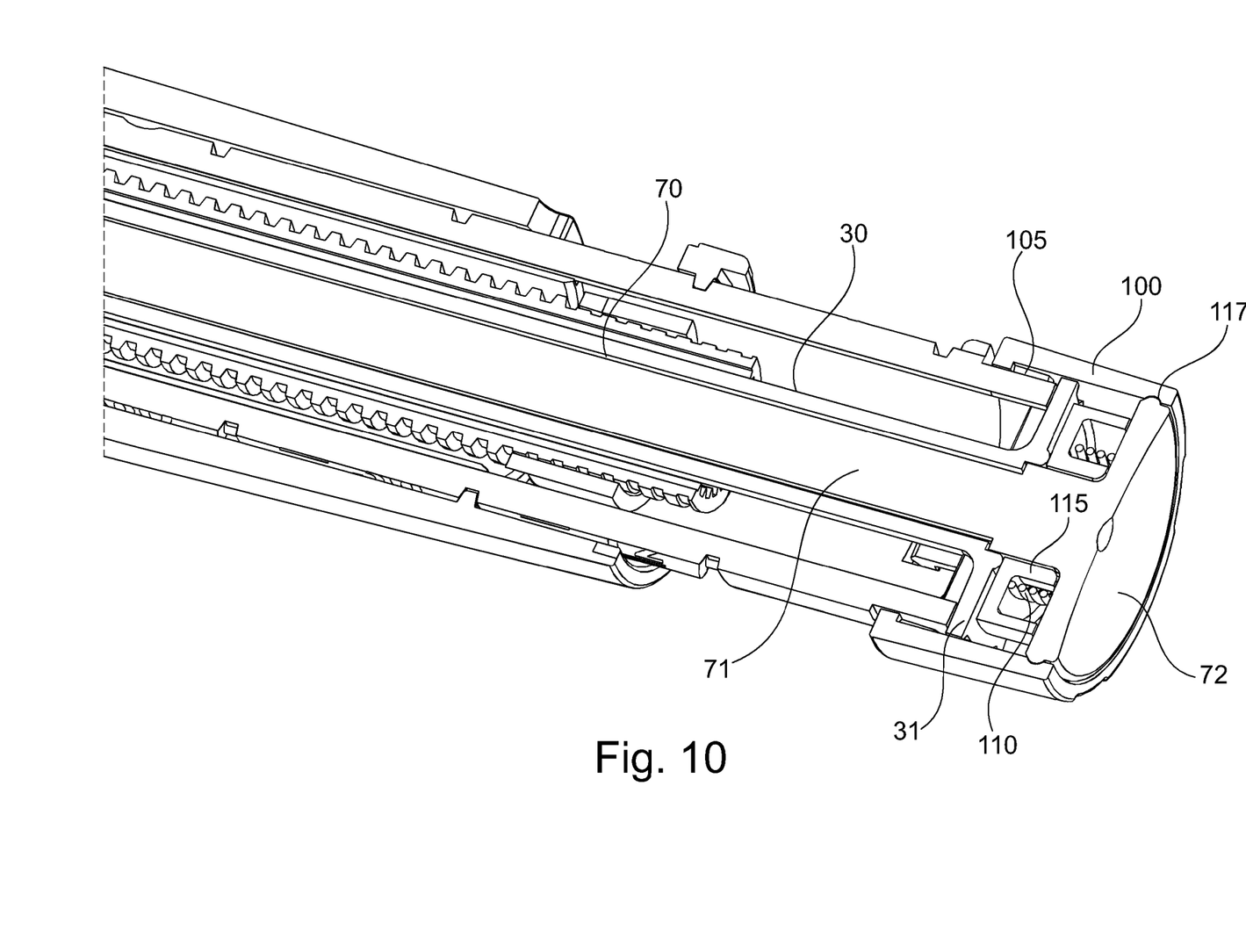
FIG. 10 shows a partial cross-sectional view of the medicament delivery device according to FIG. 1, shown during the delivery of a dose.

Thus when now the dose drum 40 and the ratchet arm drum 30 rotate, the latter will urge the plunger rod 20 to rotate as well. This rotation in the anti-clockwise direction will be allowed by the back rotating blocking element 60 due to the design of its arms 62 in contact with the ratchet 55 of the thread insert 50. The plunger rod 20 will thus rotate together with the back rotating blocking element 60, and the arms 62 of the back rotating blocking element 60 sliding over the ratchet 55 of the thread insert 50 will provide audible and tactile information. Further the rotation of the plunger rod 20 will cause it to be moved in the proximal direction due to the threaded connection with the thread insert 50, whereby the movement of the plunger rod 20 will urge the stopper 29 in the proximal direction, thereby expelling a dose of medicament through the dose delivery member. When the activator button 72 is being pressed during the delivery operation, since the dose setting knob 100 is displaced in the proximal direction together with the dose activator 70 in relation to the dose drum 40, the locking knobs 105 of the dose setting knob 100 is disengaged from the rotation locks 37 of the ratchet arm drum 30, thereby unlocking the dose setting knob 100 from the ratchet arm drum 30 (see FIG. 10). Accordingly, the dose setting knob 100 can stand still while the dose drum 40 and the ratchet arm drum 30 rotate during the injection. The dose has been delivered when the dose drum 40 has moved back to its initial position, which could be limited by some sort of blocking member (not shown) preventing further movement or rotation of the dose drum.

The device may now be removed from the dose delivery site, and the medicament delivery member discarded. If the medicament container 85 still contains a large enough dose to be delivered, the above steps may be repeated from the step "Setting operation for a dose to be delivered". In this case, after the set dose is delivered and the push button 72 is released, the dose activator spring 110 acts on the push button 72 in the distal direction, thereby securing the gap 76 between the push button 72 and the distal surface of the distal end wall 31 for the next dose delivery.

If the medicament container however contains a dose that is smaller than the prescribed dose, the present invention prevents setting a dose that is larger than the remaining dose. When the dose setting knob 100 is rotated as described above the second part 42 of the dose setting drum 40 is also rotated in relation to the plunger rod 20 and due to the threaded connection between the second part 42 and the plunger rod 20, the second part 42 is moved in the distal direction. Since, as explained above, the dose blocker ring 26 is rotationally and axially fixed to the plunger rod 20, when the maximum dose is set, the stepped portion 26-2 on the proximal side of the dose blocker ring 26 will come in contact with the radial stop 43 arranged on the inner surface of said second part 42, thereby preventing any further setting of a dose. Thus, the dose blocker ring 26 prevents any further turning of the dose setting knob 100, thereby preventing setting a dose that is larger than the remaining dose.

Preferably the device is arranged with some indicia or other information means that indicates the quantity of the last, inferior, dose so that the user may take a subsequent complementary dose with the missing volume. In this manner, also all medicament is used in the medicament container, whereby no medicament will go to waste because the remaining dose is smaller than the prescribed.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medicament delivery device, comprising:
a housing having a proximal end and a distal end;
a hollow plunger rod arranged within the housing;
a telescopic dose drum concentrically arranged between the housing and the hollow plunger rod and bidirectionally movable in relation to the housing and the hollow plunger rod when setting a dose and delivering a dose; and
a plunger rod driver configured to drive the hollow plunger rod toward the proximal end, the plunger rod driver comprising:
a hollow ratchet arm drum movably arranged within the hollow plunger rod and fixedly connected to the telescopic dose drum, wherein the hollow ratchet arm drum and hollow plunger rod are releasably coupled to each other;
a dose activator having a longitudinal rod movably arranged within the hollow ratchet arm drum, wherein the longitudinal rod and the hollow ratchet arm drum are releasably coupled to each other;
a dose setting knob fixedly connected to the dose activator and releasably coupled to the hollow ratchet arm drum; and
a resilient element between the hollow ratchet arm drum and the dose activator that biasses the hollow ratchet arm drum and dose activator in a direction decoupling the longitudinal rod from the hollow ratchet arm drum and coupling the dose setting knob with the hollow ratchet arm drum, such that during a dose setting, turning the dose setting knob forces the hollow ratchet arm drum and the telescopic dose drum to rotate together.

2. The medicament delivery device of claim 1, wherein the longitudinal rod and the hollow ratchet arm drum couple to each other against the bias of the resilient element if, after a dose is set, the dose activator moves axially toward the proximal end, thereby the hollow ratchet arm drum and the hollow plunger rod couple to each other so that the hollow plunger rod and the telescopic dose drum are displaceable toward the proximal end for delivering the set dose.

3. The medicament delivery device of claim 2, wherein the resilient element is configured to force, after delivery of the set dose, the dose activator toward the distal end, so that the dose setting knob and the hollow ratchet arm drum couple to each other and the longitudinal rod and the hollow ratchet arm drum decouple from each other, thereby decoupling the hollow ratchet arm drum and the hollow plunger rod.

4. The medicament delivery device of claim 1, wherein the resilient element includes a spring element interposed between the hollow ratchet arm drum and the dose activator and forcing the hollow ratchet arm drum and dose activator away from each other.

5. The medicament delivery device of claim 1, wherein axial movement of the dose activator toward the proximal end decouples the dose setting knob and the hollow ratchet arm drum, whereby the dose setting knob does not rotate while the dose drum rotates for delivering the dose.

6. The medicament delivery device of claim 1, wherein the dose setting knob includes locking knobs corresponding to rotation locks on the hollow ratchet arm drum.

7. The medicament delivery device of claim 6, wherein the resilient element biasses the locking knobs to couple to the rotation locks so that the dose setting knob and the hollow ratchet arm drum rotate together.

8. The medicament delivery device of claim 1, further comprising a step driver rotationally fixed and axially movable in relation to the housing, wherein the step driver comprises first slanted guide ribs that interface with a corresponding structure of the dose drum, whereby when the dose drum rotates, the corresponding structure slides over the first slanted guide ribs, thereby producing at least one of audible information and tactile information.

9. The medicament delivery device of claim 8, wherein the corresponding structure of the dose drum includes second slanted guide ribs.

10. The medicament delivery device of claim 1, wherein the telescopic dose drum includes a distal part and a proximal part that are slidably arranged relative to each other, and the distal part is arranged coaxially radially outside of the proximal part.

11. The medicament delivery device of claim 10, further comprising a step driver rotationally fixed and axially movable in relation to the housing, wherein the step driver comprises first slanted guide ribs that slide over second slanted guide ribs on the dose drum, whereby when the dose drum rotates, at least one of audible information and tactile information is produced; and the second slanted guide ribs are arranged on a proximal end of the proximal part.

12. The medicament delivery device of claim 11, wherein the step driver further includes at least one retracting arm configured to hold the proximal part and to retract the proximal part to sustain fixed increments during a dose setting.

13. The medicament delivery device of claim 10, further comprising a dose blocker member rotationally and axially fixed to the hollow plunger rod, wherein the dose blocker member is configured to interact with a stop member on the proximal part when the set dose equals a remaining dose such that rotation of the telescopic dose drum is inhibited.

14. The medicament delivery device of claim 13, wherein the dose blocker member has a ring-shaped body having at least one stepped portion on its surface facing toward the proximal end.

15. The medicament delivery device of claim 14, wherein the at least one stepped portion is configured to engage, as the hollow plunger rod moves axially, the stop member; and the stop member includes a radial stop arranged on an inner surface of the proximal part so as to prevent setting a dose larger than the remaining dose.

* * * * *